US 6,706,040 B2

(12) United States Patent
Mahon et al.

(10) Patent No.: US 6,706,040 B2
(45) Date of Patent: Mar. 16, 2004

(54) INVASIVE THERAPEUTIC PROBE (75) Inventors: John Mahon, Thousand Oaks, CA (US); Scott Rheinish, Trabuco Canyon, CA (US); Ahmad Shishegar, Woodland Hills, CA (US); John Chiu, Culver City, CA (US)

(73) Assignee: Medlennium Technologies, Inc., Los Angeles, CA (US)

( * ) Notice: Subject to any disclaimer, the term of this patent is extended or adjusted under 35 U.S.C. 154(b) by 0 days.

(21) Appl. No.: 09/992,490

(22) Filed: Nov. 23, 2001

(65) Prior Publication Data

US 2003/0100894 A1 May 29, 2003

(51) Int. Cl.[7] .............................................. A61B 18/18
(52) U.S. Cl. ........................................ 606/41; 128/898
(58) Field of Search ........................... 128/898; 606/32, 606/34, 37, 38, 39–42, 45, 33, 27–29, 30; 607/96, 98, 99, 101, 102, 105, 113

(56) References Cited

U.S. PATENT DOCUMENTS

| 3,527,227 A | | 9/1970 | Fritz ........................... 128/410 |
| 4,154,246 A | | 5/1979 | LaVeen ........................ 128/784 |
| 4,204,549 A | | 5/1980 | Pagliose ........................ 128/784 |
| 4,612,940 A | | 9/1986 | Kasevich ...................... 128/804 |
| 5,026,959 A | | 6/1991 | Ito ........................... 219/10.55 |
| 5,057,106 A | * | 10/1991 | Kasevich et al. ............. 606/33 |
| 5,097,845 A | | 3/1992 | Fetter ........................... 128/804 |
| 5,301,687 A | * | 4/1994 | Wong et al. ................. 607/116 |
| 5,358,515 A | | 10/1994 | Hurter ......................... 607/101 |
| 5,431,648 A | * | 7/1995 | Lev .............................. 606/27 |
| 5,531,662 A | | 7/1996 | Carr ............................... 600/2 |
| 5,683,382 A | | 11/1997 | Lenihan ........................ 606/33 |
| 5,776,175 A | | 7/1998 | Eckhouse ..................... 607/100 |
| 5,800,494 A | | 9/1998 | Campbell .................... 607/116 |
| 5,938,692 A | * | 8/1999 | Rudie ........................... 607/101 |
| 6,148,236 A | | 11/2000 | Dann ........................... 607/101 |
| 6,241,725 B1 | | 6/2001 | Cosman ........................ 606/41 |
| 6,306,132 B1 | | 10/2001 | Moorman et al. ............. 606/41 |
| 6,355,033 B1 | | 3/2002 | Moorman ..................... 606/33 |
| 2001/0039416 A1 | | 11/2001 | Moorman ..................... 606/33 |
| 2002/0022835 A1 | | 2/2002 | Lee ............................... 606/34 |
| 2002/0058932 A1 | | 5/2002 | Moorman ..................... 606/33 |

FOREIGN PATENT DOCUMENTS

| JP | 5-23400 | 2/1993 | ............. A61N/5/02 |
| JP | 5-76610 | 3/1993 | ............. A61N/5/02 |

* cited by examiner

Primary Examiner—John P. Leubecker
Assistant Examiner—Peter J Vrettakos
(74) Attorney, Agent, or Firm—Sheppard, Mullin, Richter & Hampton LLP (57) ABSTRACT An invasive therapeutic probe assembly and related methods for application of RF energy to a volume of body tissue are provided. The probe assembly includes an RF source configured to provide an RF energy having selected characteristics, a probe having a probe shaft and an antenna positioned therein, and a feed line for providing conductivity from the RF source to the antenna probe. The probe assembly is adapted to generate a zone of therapeutic effectiveness having a selected geometry and volume. The related method includes positioning the probe in a selected location with reference to a target tissue, initiating an electromagnetic field from the antenna having a selected geometry, and producing a zone of therapeutic effectiveness having a selected geometry and volume. The producing step preferably includes, taking periodic temperature measurements from sensors positioned at a selected location, and manipulating the selected characteristics of the RF energy to include duration and/or power level.

23 Claims, 5 Drawing Sheets

INVASIVE THERAPEUTIC PROBE

BACKGROUND OF THE INVENTION

The present invention relates generally to invasive probes for therapeutic purposes and, more particularly, to invasive probes and related methods for hyperthermia treatment and ablation of body tissue.

Probes configured for generally localized radiation of electromagnetic energy at radio frequencies, i.e., RF energy, have been beneficially used to heat body tissue for therapeutic purposes. Typically, a probe is positioned in proximity to the target tissue via insertion through a small incision. One such purpose is in the treatment of cancerous tumors, which are particularly susceptible to damage at elevated temperatures resulting from exposure to RF energy. The application of sufficient energy will result in necrosis of the tumor, e.g., necrosis of cancerous tumor cells generally occurs once heated above a certain temperature threshold (about 50 to 55 degrees Celsius). For other purposes, such as in various hyperthermia treatments, a lower temperature threshold is typically used. Nonetheless, for a probe to be effective, it must radiate sufficient energy to raise the temperature of the target tissue above the prescribed temperature threshold.

However, viable tissue neighboring the target tissue can be damaged by excessive heating through overexposure to RF energy. In some therapeutic applications beneficial results can still be achieved even with relatively significant incidental damage to viable tissue. Although, in certain therapeutic applications, even minimal damage to viable tissue can result in grave harm to the patient, e.g., in the treatment of brain tumors. Thus, for an RF probe treatment to be permissible in certain applications, the probe must be able to deliver sufficient localized energy to effect necrosis of the tumor while minimizing damage to viable tissue. With the benefits of an MRI machine, detailed information about the target tumor can be obtained such as its position, orientation, shape, and volume. Frequently, tumors have a generally spherical shape. Traditional probe designs have been generally effective in certain applications, but, in other applications, the risk of damage to viable tissue has been too great for them to be a practical treatment option, particularly if a precise zone of therapeutic effectiveness is needed.

It is, therefore, an object of this invention to provide an improved probe configured to generate a predetermined zone of therapeutic effectiveness having a selected geometry and volume, to include substantially spherical shapes, for use in heating a target region of tissue such as in hyperthermia treatment and ablation of tumors.

Other objects of this invention include making the probe low cost so it can optionally be disposed after a single use and configuring the probe to allow MRI imaging to discern the probe placement and position without unduly interfering with image quality.

These and other objects of the invention will be understood more particularly from the following description taken in conjunction with the accompanying drawings.

SUMMARY OF THE INVENTION

An invasive probe assembly is provided for application of RF energy to a volume of body tissue. The probe assembly includes an RF source configured to provide an RF energy having selected characteristics, a probe having a probe shaft and an antenna positioned therein, and a feed line for providing conductivity from the RF source to the antenna probe. The probe assembly is adapted to generate a zone of therapeutic effectiveness having a selected geometry and volume.

The antenna preferably is a dipole antenna having a first dipole region located at the distal end of the probe shaft and a second dipole region located proximate thereto along the probe shaft. A choke having selected characteristics to inhibit excessive current flow back and excessive heating of the feed line is preferably located at the second dipole region.

The invention also resides in a method of heating body tissue for a therapeutic purpose. In this method, a probe assembly, including a probe with an antenna, an RF source, and a feed line, is used. The method includes positioning the probe in a selected location with reference to a target tissue, initiating an electromagnetic field from the antenna having a selected geometry, and producing a zone of therapeutic effectiveness having a selected geometry and volume.

The producing step preferably includes, taking periodic temperature measurements from sensors positioned at a selected location, and manipulating the selected characteristics of the RF energy to include duration and/or power level.

The invention further resides in a method of making an invasive probe having a dipole antenna and a feed line adapted to connect the dipole antenna to an RF source. The method comprises fitting an insulator having selected characteristics over the feed line at a selected location along the feed line; and fitting a radiating sleeve having selected characteristics over the dielectric sleeve and the feed line such that the sleeve is connected to an outer conductor of the feed line at a distal end and left open at a proximate end, thereby forming a choke.

Other features and advantages of the invention should become apparent from the following description of the preferred embodiment, taken in conjunction with the accompanying drawings, which illustrate, by way of example, the principles of the invention.

BRIEF DESCRIPTION OF THE DRAWINGS

Embodiments of the present invention will now be described, by way of example only, with reference to the following drawings in which.

DESCRIPTION OF THE PREFERRED EMBODIMENTS

In this section, the present invention is described in detail with regard to the figures briefly described above. As such, the following terms are used throughout the description. For purposes of construction, such terms shall have the following meanings:

The term "target tissue," unless otherwise specified, shall refer to a volume of tissue, such as a tumor, intended to be heated to bring about a desired therapeutic result.

The term "zone of therapeutic effectiveness," unless otherwise specified, shall refer a volume of tissue, the surface of which is defined by a selected threshold temperature along a temperature gradient within the tissue, wherein substantially all tissue therein is raised above a desired threshold temperature.

Figure 1:
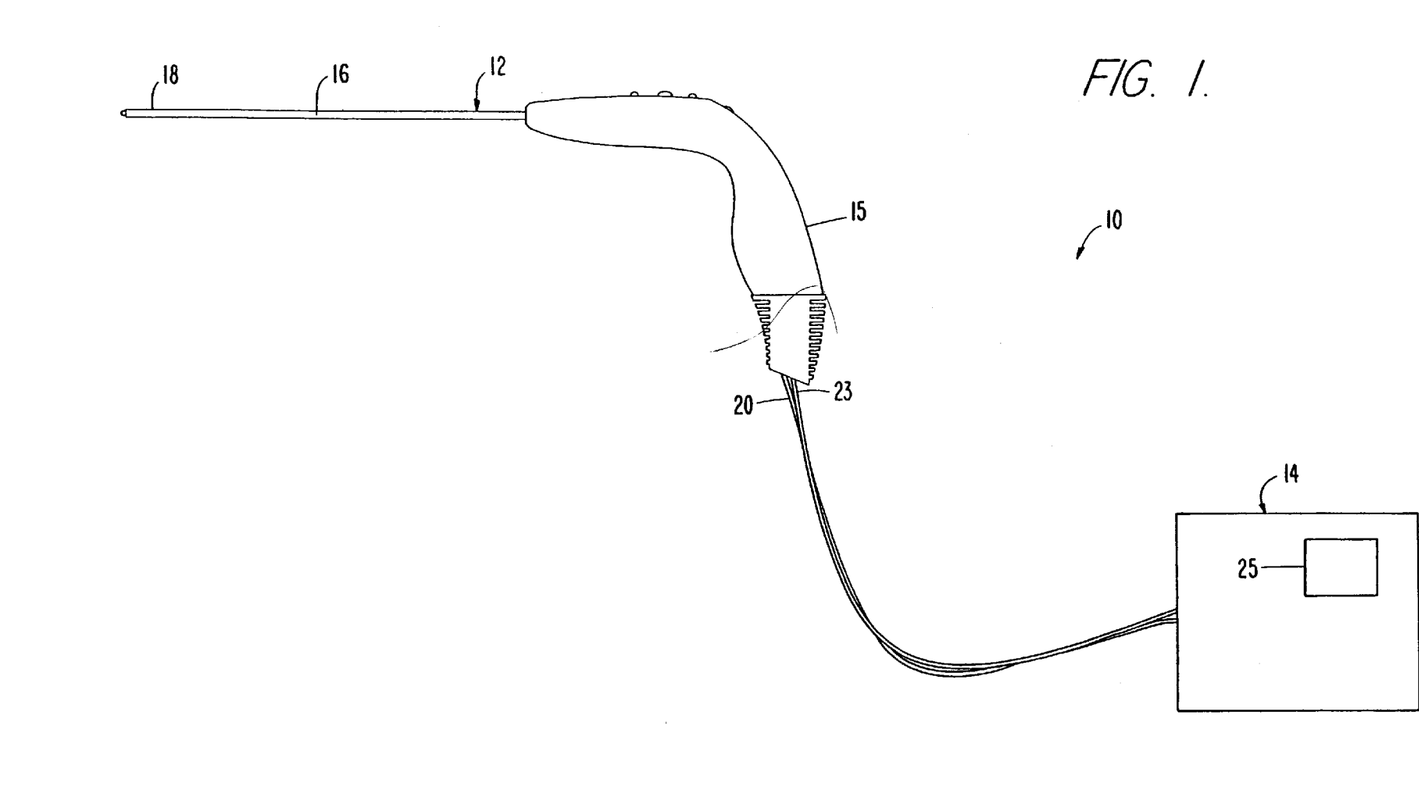
FIG. 1 is a block diagram of a probe assembly depicting an RF source connected to a probe in accordance with the invention.
Figure 2:
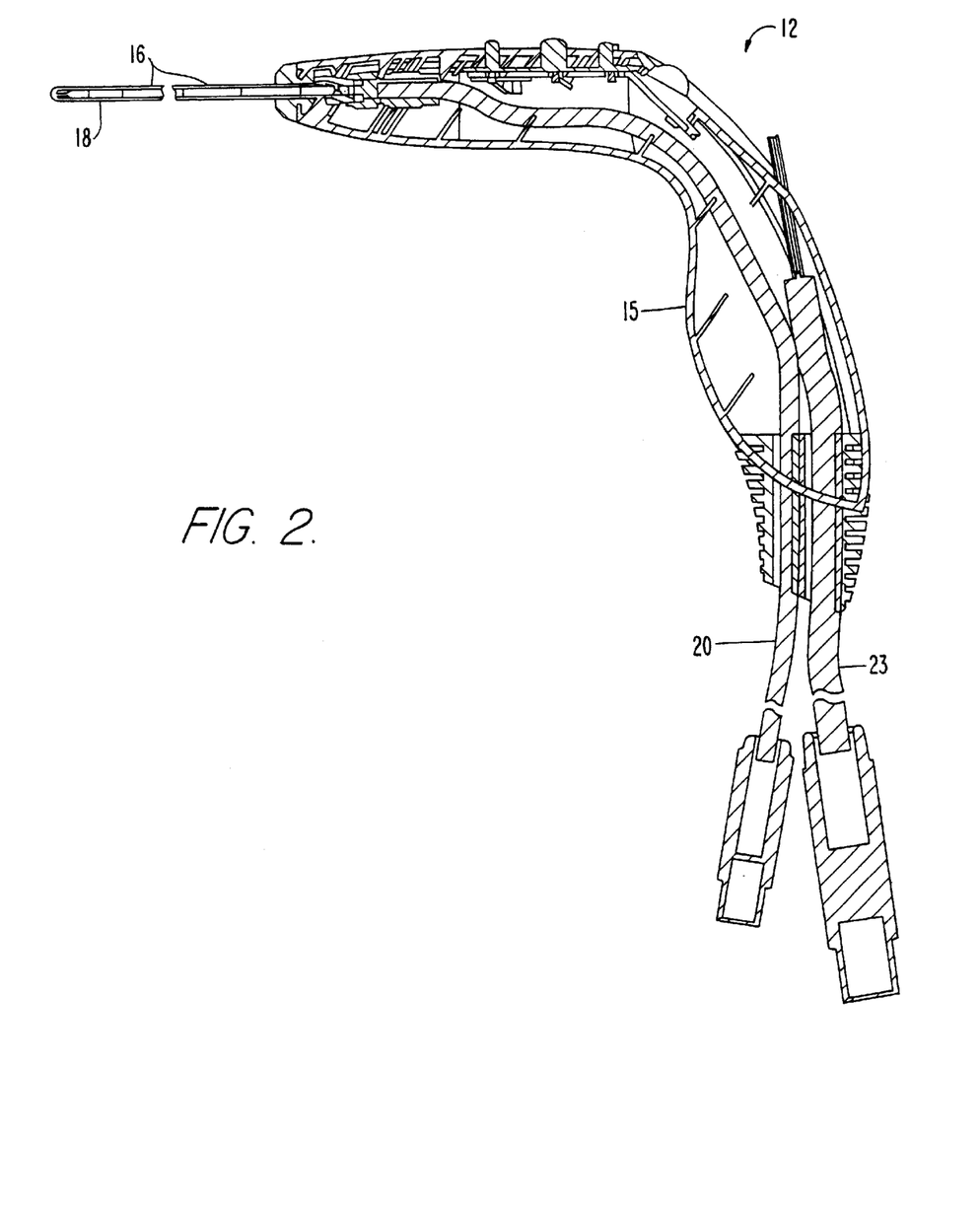
FIG. 2 is a cross sectional view of the probe of FIG. 1.

With reference now to the illustrative drawings, and particularly to FIG. 1, there is shown a preferred embodiment of a probe assembly 10 in accordance with the present invention having a probe 12 connected to an RF source 14. With reference to FIG. 2, the probe has a handle 15, a probe shaft 16 projecting from the handle, a dipole antenna 18 located at the distal end of the probe shaft (for convenience of reference, this region is also referred to as a probe tip), and a feed line 20 for providing conductivity from the RF source to the dipole antenna. The probe can be constructed primarily from non-ferromagnetic material, for compatibility with MRI machines. The feed line is connected to the antenna at a location referred to as a slot 22.

The outer coating 44 of probe 12 is formed of an electrically non-conductive material. It seals the internal antenna elements from exposure to bodily fluids, and it forms a smooth surface that facilitates insertion and removal of probe. For example, a biocompatible material with low loss at microwave frequencies such as such as Paralyne™ can be used. Optionally, the probe assembly can be disposed after each procedure. The feed line 20 is detachable at a selected point along its length to facilitate disposal. The probe is also configured with indicator lights and an activation button (FIG. 2A) connected via conductors 23 to a controller 25 for controlling the RF source 14 (FIG. 1). This configuration affects ease of use and interoperability with MRI machines, allowing the RF source to be placed a distance away from the MRI machine.

The probe assembly 10 is useful for a range of therapeutic applications to include ablation and/or necrosis of cancerous tumors, particularly, tumors having a generally spherical shape. The probe assembly is configured and operated in such a fashion as to produce a zone of therapeutic effectiveness having geometry that substantially matches the geometry of the tumor. Several factors are accounted for in manipulating the zone of therapeutic effectiveness to include the RF energy's frequency and power level, the antenna's dimensions, properties of probe materials, and properties of the target tissue. These factors will be discussed in detail below.

Figure 2A:
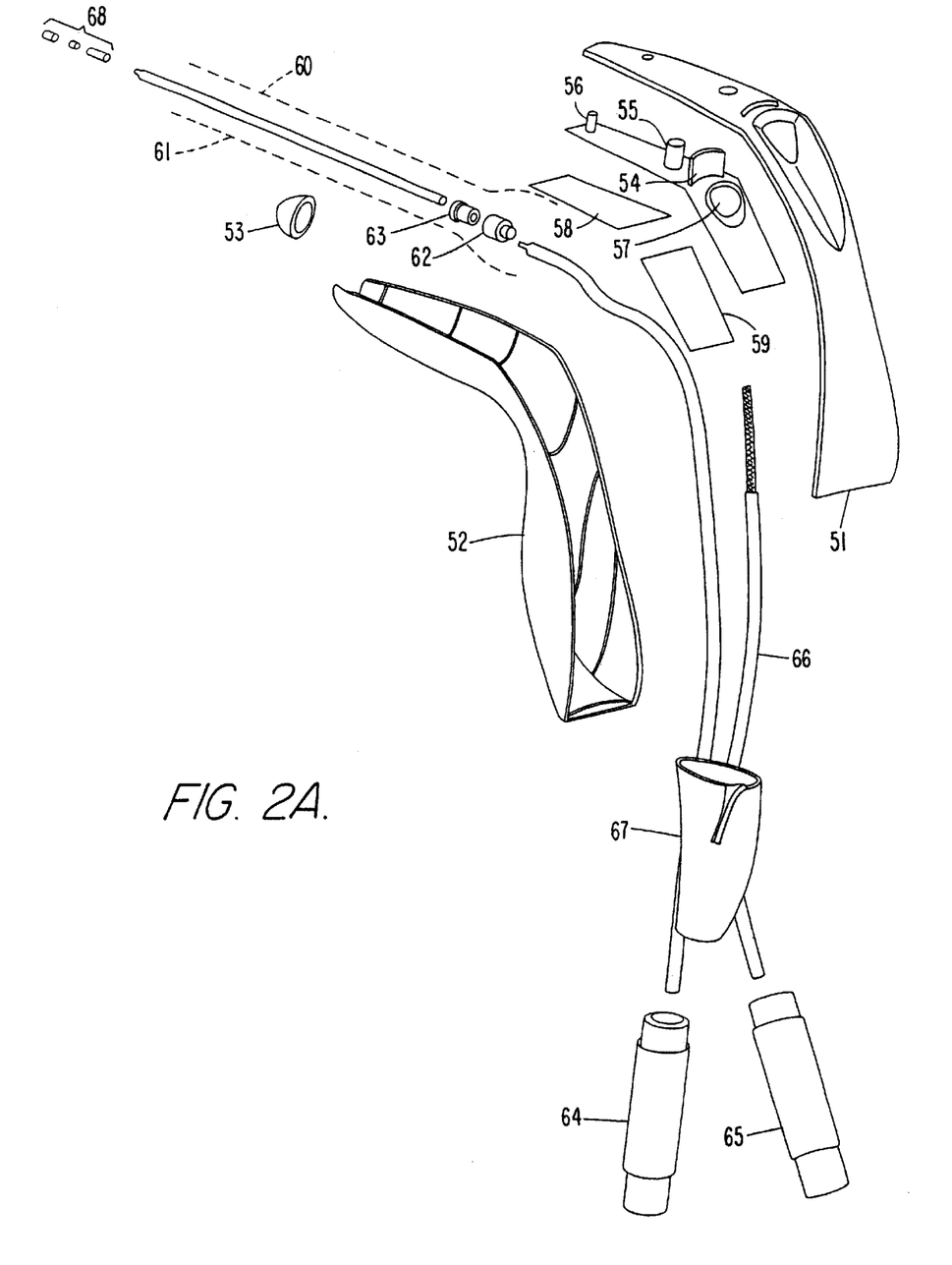
FIG. 2A is an exploded perspective view of the probe shown in FIG. 2.

With reference now to FIG. 2A, the probe handle 15 (FIG. 2) includes a handpiece top 51, a handpiece bottom 52 and a strain relief tip 53 located at a distal end of the handle. The probe 10 further includes several indicator lights positioned atop the probe for easy viewing by the user, to include, a microwave on light indicator 54 that illuminates upon powering on the probe, an arm button armed indicator 55 that illuminates when the probe is ready to use and a fault indicator 56 that illuminates to warn the user of a fault with the system. An activation button 57 is further provided, allowing the user to activate the probe by pressing the button. The indicators and the activation button are mounted to circuit boards 58 and 59.

The probe shaft 16 (FIG. 2) is configured with a temperature sensing device having first and second thermistors 60, 61. In this embodiment, the feed line 20 includes a coaxial cable and a connector 64 for providing detachable connection to the RF source 14. The connector includes a female connector 62 and a male connector 63 to continue the conductivity from the connector 64 out to the probe tip 68. Connector 65 attaches to the bundled wire 66 to provide power to the indicators (54, 55, 56) and activation button 57. The strain relief base 67 disposed about the lower portion of the handle.

Figure 3:
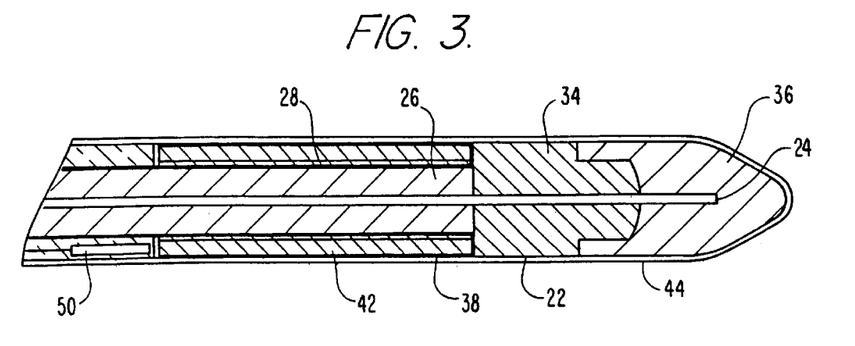
FIG. 3 is cross sectional view of a first embodiment of a probe tip depicting a choke formed by folding back a selected length of the outer conductor of the feed line in accordance with the invention.

Now with reference to FIG. 3, a detailed illustration of a preferred embodiment of the probe tip is provided. This embodiment of the probe tip is configured for use with an RF source 14 (FIG. 1) having an adjustable output power range from 30 to 300 watts that provides an RF energy having a frequency (f) of 2.45 GHz, which is within the Instrumentation, Scientific and Medical band as established by the Federal Communications Commission. The feed line 20 provides conductivity from the RF source and terminates in the dipole antenna 18 at the slot 22. In this embodiment, the feed line is a semi-rigid coaxial cable of 50 ohms characteristic impedance having a center conductor 24, an insulator 26, and an outer conductor 28. Other suitable transmission means alternatively may be used.

The dipole antenna 18 has two one-quarter wavelength ($\lambda$/4) dipole wings that are referred to as first and second dipole regions 30 and 32, respectively. The first dipole region is located at the distal end of the probe shaft 16 and the second dipole region is located proximate thereto along the probe shaft. The first and second dipole regions define the dipole axis. A spacer 34 formed of a dielectric material, such as a polycarbonate, is positioned between the first and second dipole regions. The first dipole region includes a dipole cap 36 formed of a metallic or metallically coated material, preferably a non-ferromagnetic material having sufficient radiating properties. One suitable material is brass. The center conductor 24 extends beyond the insulator 26 and the outer conductor 28 and is connected to the dipole cap.

The second dipole region 32 includes a choke 38 having a radiating skirt 40 connected to the outer conductor 28 and an insulator 42 positioned therebetween. In this embodiment, the choke is formed by exposing a selected length of the outer conductor at the terminal end of the coaxial feed line and folding it back onto itself, forming the skirt, and sandwiching the insulator. Beneficially, the insulator has an appropriate length to achieve a sufficiently high reactive impedance between the feed line 20 and the skirt to protect against excessive current flow back and excessive heating of the feed line. In this embodiment, the insulator is provided a length set at approximately one-fourth of the energy's wavelength as it propagates through the insulator ($\lambda_1$/4), wherein $\lambda_i$, equals the speed of light (c) divided by the product of RF frequency (f) times the square root of the dielectric constant of the insulator ($\epsilon$).

$$\lambda_1 = c/(f\sqrt{\epsilon})$$

The RF frequency is 2.45 GHz and the insulator is formed of a ceramic having a dielectric constant ranging between 9 and 10. In this embodiment, the insulator is configured to have a length of approximately one centimeter. The length can be adjusted to account for capacitive effects at the opening of the choke. In other embodiments, the insulator is formed of different materials having varying dielectric constants, thereby which beneficially aiding in manipulating the geometry of the zone of therapeutic effectiveness produced by the probe assembly 10.

Figure 4:
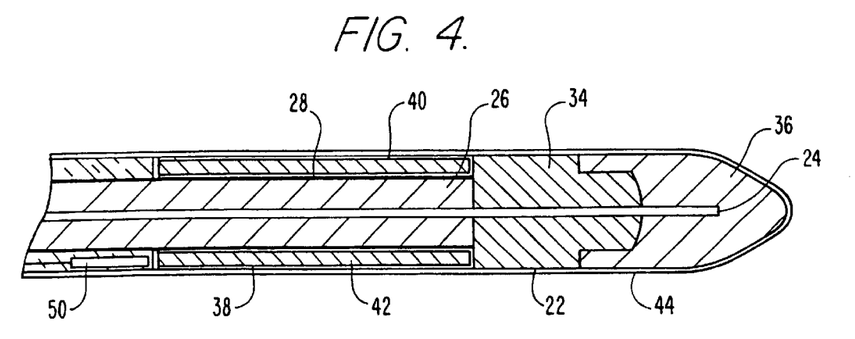
FIG. 4 is cross sectional view of a second embodiment of a probe tip depicting a choke formed by pressfitting a radiating skirt over an insulator in accordance with the invention.

FIG. 4 shows an alternate embodiment of the choke 38. In this embodiment, the choke is formed by metallically coating the insulator 42 with selected conductive material to a desired thickness. The choke is configured such that the proximate end of the choke is void of metallic coating, forming an open end. This can be achieved in various ways. For example, the insulator can be completely coated with metallic material, then the coated insulator can be cut to a selected length at the proximate end. The choke is then fitted over the feed line with the outer conductor 28 in contact with the metallic coating on the inner surface of the choke.

The dipole antenna 18 is configured to generate a range of heating patterns, i.e., temperature gradients, within body tissue generally having ellipsoidal shapes to include spherical shapes. These heating patterns result, chiefly, from the effects of the antenna's far and near electric fields (collectively the net electric field). Generally, dipole antennas produce a far electric field having a shape resembling a symmetric torus aligned about the antenna's dipole axis. The near electric field is also symmetric about the dipole axis and is located adjacent to the first and second dipole regions, 30 and 32, and the slot 22. In invasive treatment applications, the effects of the near electric field are relatively pronounced due to the lossy nature of body tissue.

More specifically, factors that aid in manipulating the ellipsoidal shape of the resulting heating pattern are the lengths of the dipole regions 30 and 32, the radii of various components, the power delivered to the probe, the frequency of operation, and the electrical properties of the tissue. The power level of the RF energy provided by the RF source 14 varies the relative contribution of the far field and near field radiation to the resulting heating pattern. At relatively lower power levels, the near electric field has a more pronounced impact on the heating pattern's shape than it does at relatively higher power levels.

Various configurations for the dipole antenna can be utilized in accordance with the invention to manipulate the shape of the resulting heating pattern.
The lengths of the two dipole halves also contribute to the length of the heating pattern's shape. The length of the material inside the choke and its dielectric constant are configured in a manner as discussed above. The length of the first dipole region can be lengthened or shortened as desired to better shape the pattern.

There also exists a relationship between this length and the impedance of the dipole and the ratio of the power reflected back along the input coaxial cable with respect to the incident power. The reflected power can be reduced with a matching circuit along the feed line proximate to the antenna. Alternatively, since the power required by the tumor ablation process is small, i.e., 20–50 watts and since common RF generators can deliver large amounts of power, one can allow the ratio of the reflected power to be larger than ideal. The RF source can be protected by the inclusion of an isolation circuit such as those having a circulator.

The temperature of a discrete amount of tissue resulting from exposure to an electric field can be expressed formulaically. It is a function of the probe's electric field strength at that point, tissue characteristics, and duration of energy application. Pennes' Bio-Heat Transfer equation relates the temperature distribution ($\partial T/\partial t$) to absorbed power density of tissue (P), tissue and blood specific heat (c and $c_b$), blood temperature $T_b$, blood perfusion rate ($W_b$), tissue density (r), and tissue thermal conductivity $\kappa$, as expressed in the following:

$$\rho c(\partial T/\partial t) = \nabla(\kappa \nabla T) - W_b c_b (T - T_b) + P$$

The tissue's absorbed power density as a function of the electric field is related to electrical conductivity ($\sigma$) as expressed in the following:

$$P = \sigma/2 * |E|^2$$

Pennes' Bio-Heat Transfer equation can be solved numerically by standard methods such as Finite Element Analysis with the benefit of real time temperature measurement data.

The electric field at a given point within a medium can generally be expressed as a function of the electric field intensity at the antenna ($E_o$), distance from the antenna (r), and the tissue's dielectric characteristics ($\alpha + j\beta$):

$$E = (E_o e^{-(\alpha+j\beta)r})/r^2$$

Several analytical approaches for analyzing a dipole antenna's electric field intensity as a function of the antenna's configuration and the propagation medium are known in the art. These analytical methods, to include, Method of Moments Analysis (MoM), Finite Difference Time Domain technique (FDTD), Transmission Line Modeling (TLM), and Finite Element Method (FEM), are used to model complex antenna configurations and complex mediums.

Modeling of an embodiment revealed an electric field pattern having a spherical shape of 2.5 cm radius at −20 db of power absorption. The power level needed to achieve the desired temperature at the sphere's surface or boundary can be calculated using Pennes' Bio-Heat Transfer function discussed above. The source power level can then be adjusted accordingly to account for transmission, interconnection and reflection losses with the benefit of real time temperature measurement data.

Figure 5:
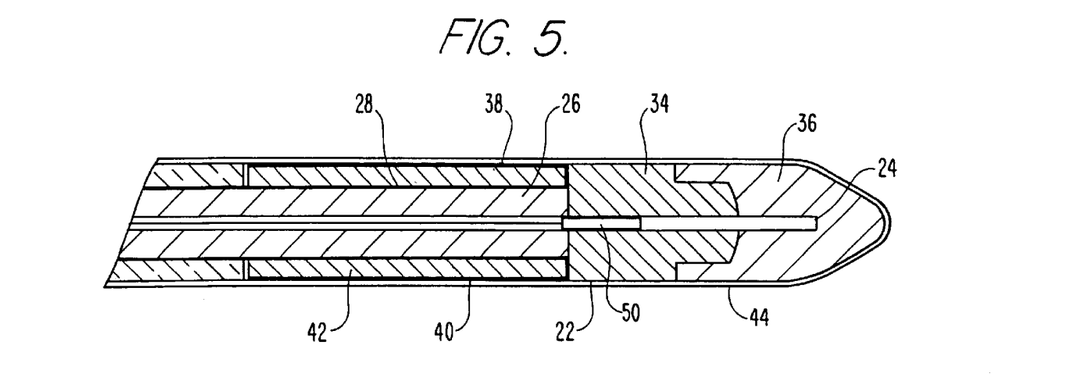
FIG. 5 is cross sectional view of a third embodiment of a probe tip with a hollow center conductor illustrating temperature sensor placement.

Thus, a predetermined zone of therapeutic effectiveness can be achieved and controlled in real time to a predefined level and for a predefined duration as needed for a given treatment. The temperature sensing can be accomplished by use of thermocouple, thermistor, RTD, optical sensors or other methods. As shown in FIG. 5, the center conductor 24 is hollow, and a sensor 50 is positioned therein. Beneficially, the RF source can operate in an intermittent mode, i.e., it will not radiate RF energy for selectably spaced durations, aiding in increased accuracy of the temperature measurements.

Figure 6:
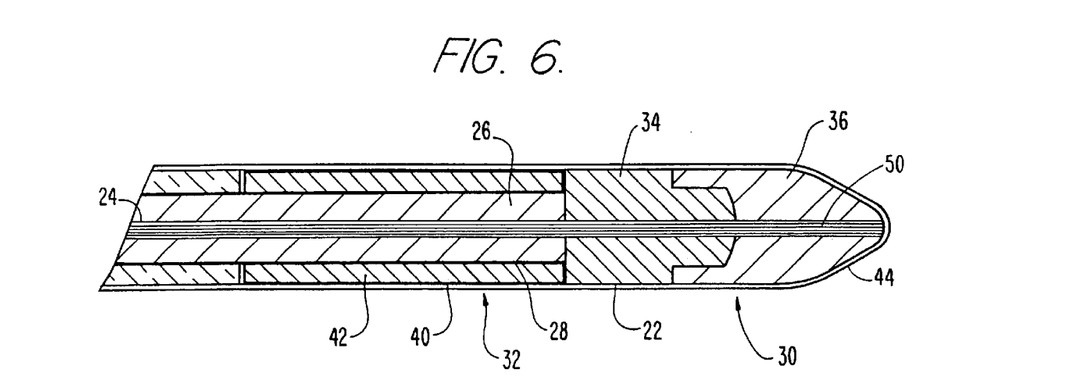
FIG. 6 is cross sectional view of a fourth embodiment of a probe tip depicting a hollow center conductor with optical elements therein extended to the metallic or metallically coated distal end.

As shown in FIG. 6, the hollow center conductor extends to the distal end of the probe shaft and optical strands 50' are positioned therein. In this embodiment, the outer coating 44 of the probe 12 can be select to be transparent to light source frequencies. The optical strands can be utilized for a variety of beneficial purposes, such as, temperature measurement and tissue imaging. For example, a selected number of strands may be allocated for optical temperature sensing with other strands allocated for imaging. Both wide-band light and narrow band light, e.g., laser, may be used for tissue imaging.

The foregoing detailed description of the present invention is provided for the purposes of illustration and is not intended to be exhaustive or to limit the invention to the precise embodiments disclosed. Accordingly, the invention is defined only by the following claims.

We claim:

1. An invasive probe assembly for therapeutic treatment, the probe assembly comprising:

a coaxial feed line having an inner conductor, an outer conductor, and an insulating sleeve axially surrounding the outer conductor, the feed line configured for electrical contact to an RF source configured to provide RF energy having selected characteristics including a prescribed operating frequency; and a probe having a rigid probe shaft and an antenna positioned therein, the antenna including
  a first dipole region at a distal end of the probe shaft and connected to the inner conductor of the feed line, the first dipole region having a rounded metallic tip,
  a second dipole region proximally spaced therefrom, forming a dipole axis, the second dipole region having
    a radiating skirt electricalliy connected at a distal end to the outer conductor of the feed line and therefrom axially spaced from the outer conductor to a proximal end the skirt, and
    a cylindrical insulator disposed between the outer conductor and the skirt, thereby forming a choke at the prescribed operating frequency; wherein the length of the choke is substantially a quarter wavelength as determined for propagation of the provided energy through the cylindrical insulator, and
    a structural spacer formed of dielectric material disposed between the dipole regions along the dipole axis.

2. An invasive probe assembly as defined in claim 1, wherein the skirt and cylindrical insulator are a unitary piece in which the skirt is a metallic coating disposed on a first end and on an outer side surface of the cylindrical insulator.

3. An invasive probe assembly as defined in claim 2, wherein:
  the insulating sleeve of the feed line terminates prior to the cylindrical insulator, and
  the metallic coating is further disposed in an axial bore defined by the cylindrical insulator.

4. An invasive probe assembly as defined in claim 1, wherein the dielectric spacer is formed of polycarbonate and defines an axial bore sized to allow the inner conductor to extend therethrough.

5. An invasive probe assembly as defined in claim 1, wherein the cylindrical insulator has a dielectric constant between about 9 and 10 and the prescribed operating frequency is about 2.45 GHz.

6. An invasive probe assembly as defined in claim 5, wherein the choke has a length of about 1 cm.

7. An invasive probe assembly for therapeutic treatment, the probe assembly comprising:
  a coaxial feed line having an inner conductor, an outer conductor and an insulating sleeve axially surrounding the outer conductor, the feed line configured for electrical contact to an RF source configured to provide RF energy having selected characteristics including a prescribed operating frequency; and
  a probe having a rigid probe shaft with an antenna positioned therein, the antenna including,
    a first dipole region located at a distal end of the probe shaft and connected to the inner conductor of the feed line,
    a second dipole region proximally spaced therefrom, forming a dipole axis, the second dipole region having
      a radiating skirt electrically connected at a distal end to the outer conductor of the feed line and therefrom axially spaced from the outer conductor to a proximal end the skirt, and
      a cylindrical insulator disposed between the outer conductor and the skirt, thereby forming a choke at the prescribed operating frequency; wherein the length of the choke is substantially a quarter wavelength as determined for propagation of the provided energy through the cylindrical insulator, and
    a structural spacer formed of dielectric material disposed between the dipole regions along the dipole axis, the spacer defining an axial bore allowing the inner conductor to extend therethrough.

8. A probe assembly as defined in claim 7, wherein the center conductor is hollow and optical strands are positioned therein.

9. A probe assembly as defined in claim 8, wherein a selected number of the optical strands are allocated for optical temperature sensing.

10. A probe assembly as defined in claim 8, wherein a selected number of the optical strands allocated for imaging.

11. An invasive probe assembly as defined in claim 7, wherein the skirt is a portion of the outer conductor folded back over the cylindrical insulator.

12. An invasive probe assembly as defined in claim 11, wherein the first dipole region is a metallic cap having a rounded tip tapering to a cylindrical portion.

13. An invasive probe assembly as defined in claim 12, wherein the cylindrical portion of the cap defines a rearwardly facing recess and the structural spacer includes a portion disposed within the recess.

14. An invasive probe assembly as defined in claim 13, wherein the skirt and cylindrical insulator are a unitary piece in which the skirt is a metallic coating disposed on a first end and an outer side surface of the cylindrical insulator.

15. An invasive probe assembly as defined in claim 14, wherein:
  the insulating sleeve of the feed line terminates prior to the cylindrical insulator, and
  the metallic coating is disposed in an axial bore defined by the cylindrical insulator.

16. An invasive probe assembly as defined in claim 7, wherein the cylindrical insulator is formed of ceramic.

17. An invasive probe assembly as defined in claim 16, wherein the choke has a length of about 1 cm.

18. A method of heating body tissue, the method comprising:
  positioning a probe in a selected location with reference to a target tissue, the probe having an antenna therein that receives RF energy from an RF source, the antenna including first and second dipole regions forming a dipole axis and a structural spacer formed of dielectric material disposed between the dipole regions along the dipole axis; wherein the first dipole region has a rounded metallic tip, a second dipole region has a radiating skirt and a cylindrical insulator thereby forming a choke having a length substantially a quarter wavelength as determined for propagation of the provided energy through the cylindrical insulator;
  initiating an electric field from the antenna having a selected geometry; and producing a zone of therapeutic effectiveness having a selected geometry and volume.

19. A method as defined in claim 18, wherein the producing step further includes taking periodic temperature measurements from sensors positioned at a selected location, and manipulating selected characteristics of the RF energy to include duration and/or power level.

20. A method of making an invasive probe having a dipole antenna and a feed line adapted to connect the dipole antenna to an RF source, the method comprising:
  providing a first dipole region formed of an insulator having a cylindrical shape with a predetermined thickness and length, and having a conductive material coated thereon such that the insulator is substantially covered with conductive material and the proximal end of the insulator is void of conductive material;

fitting the coated insulator at a selected location along the feed line such that it is in contact with an outer conductor of the feed line thereby forming a choke;

placing a structural spacer of dielectric material forward of the first dipole region such that an inner connector of the feed extends through an axial bore thereof; and placing a second dipole region forward of the structural spacer and in electrical contact with the inner conductor.

21. A method as defined in claim 20, wherein the insulator is ceramic.

22. A method as defined in claim 20, further including the step of selecting dimensions and materials for the antenna to effectuate a zone of therapeutic effectiveness having a selected geometry and volume.

23. A method as defined in claim 20, wherein the providing step further includes the steps of coating all surfaces of the insulator with conductive material to a selected thickness, and cutting the coated insulator to a selected length, and thereby providing the insulator with a proximal end void of conductive material.

* * * * *